United States Patent [19]

Gottsdanker

[11] 4,015,343
[45] Apr. 5, 1977

[54] TESTING APPARATUS

[76] Inventor: Robert M. Gottsdanker, 100 E. Constance, Santa Barbara, Calif. 93105

[22] Filed: Mar. 29, 1976

[21] Appl. No.: 671,244

[52] U.S. Cl. ............................ 35/22 R; 35/6; 35/9 H; 197/182

[51] Int. Cl.² ................................ G09B 19/00

[58] Field of Search ............ 35/6, 9 R, 9 H, 22 R, 35/48 R; 197/180, 182

[56] References Cited

UNITED STATES PATENTS

| | | | |
|---|---|---|---|
| 427,688 | 5/1890 | Hooper | 197/182 |
| 1,319,687 | 10/1919 | Bates | 35/6 |
| 1,866,582 | 7/1932 | Smith | 197/182 |
| 2,802,284 | 8/1957 | Orelsonstok et al. | 35/6 |
| 3,162,959 | 12/1964 | Woolman | 35/6 X |
| 3,281,959 | 11/1966 | Kobler et al. | 35/6 |
| 3,423,845 | 1/1969 | Edge et al. | 35/6 |
| 3,497,966 | 3/1970 | Gaven | 35/6 X |
| 3,611,586 | 10/1971 | Kuramdcht | 35/6 |
| 3,675,339 | 7/1972 | LaMarca | 35/6 |
| 3,701,975 | 10/1972 | McBride | 35/6 |
| 3,720,298 | 3/1973 | Alonas et al. | 197/182 |
| 3,729,836 | 5/1973 | Mayeda | 35/6 |
| 3,769,719 | 11/1973 | Meister | 35/6 |
| 3,779,635 | 12/1973 | Yevick et al. | 197/180 X |

*Primary Examiner*—William H. Grieb
*Attorney, Agent, or Firm*—Harry W. Brelsford

[57] ABSTRACT

A person being tested looks into a mirror through which is exhibited on a surface displaced upwardly from the striking row a previously prepared sheet of paper inserted into a conventional typewriter. The path of viewing passes through a Dove prism or other optical system to rotate optically the material prepared in miniature on the paper. The prepared material may be in miniature letters, symbols, etc., and is viewed through a magnifying lens which permits clear visibility of the miniature material. The optical rotation permits the commands or stimuli on the paper to be prepared in a vertical orientation and yet be viewed in any surface orientation, notably as horizontal words, letters, or numbers. Other symbols, lines, shapes, designs, textures, pictures, or colors may also be used as commands. A clock is actuated with the subject's first response on a row and is stopped at completion of the row of typing. The person being tested then responds by typing the correct answer to the command or task viewed by him through the optical system.

6 Claims, 5 Drawing Figures

TESTING APPARATUS

DISCLOSURE

My invention relates to psychological testing, experimentation, and training, and has particular reference to visual stimulation and motor response wherein the subject presses keys on a typewriter as the motor response mechanism.

Psychological testing, experimentation, and training takes many forms. The present apparatus is used wherein the subject is presented with a visual stimulus as a command and the response is manual in the form of typewriting letters, numbers, words, other characters, or combinations of these. The present apparatus will be described with reference to a previously prepared sheet of paper upon which various indicia have been applied as by writing, printing, or photocopying. These indicia define the command or the task to be completed by the person operating the apparatus.

For example, the subject may have a visual command in the form of a letter and number "L4" and interprets this, according to a previous instruction on the code, to press the typewriter key with the index finger or fourth finger of his left hand. It is not necessary for the subject to be familiar with typewriting; he need simply be instructed on which set of keys to rest his fingers. If he makes the correct response, he will type the letter "f"; and after finishing a series of tasks his worksheet can be examined to determine the correctness of his response. The grading of the subject's responses is speeded up by applying to the same sheet (but hidden from the sight of the subject) the correct response. By proper registry of the paper in the typewriter, the subject's response can be typed adjacent to (displaced vertically from) the previously established correct response, and a quick visual comparison by the tester will permit easy grading. Tasks of any complexity can be devised, and the foregoing is merely a simple illustration. An electric clock is started with the first response on a row and is stopped with the last response on the row.

I have devised an optical system, timing system, and typewriter combination for such testing. In summary, a person being tested sits at a typewriter and looks into an optical system disposed above the platen of the typewriter. He views a sheet of paper in the typewriter bearing one or more command letters, numbers, other symbols, or other stimuli; and as he types his response new command indicia come into view so that he may continue his response until he reaches the end of a line of typewriting. The typewriter is thereupon automatically or manually operated to present a new line of command indicia and a clean striking line on the sheet of paper for the subject's responses. The optical system is adjustable to limit the view of the subject to one, two, or more commands at any one time; they may include, in addition to the present command, both preceding and forthcoming commands.

Usually, it is desirable to increase the number of indicia per command, which can be done by placing them in reduced size in a vertical columnar array. In order to correct for the miniaturization and change in directional orientation, I have included in my optical system devices for making these vertical columnar commands appear to be large and horizontal to the subject being tested. Accordingly, the apparatus includes a magnifier and a selective optical rotational device. Since the image is in inverted form, it must be corrected. This is accomplished by a viewing mirror which presents the subject with a normal image.

The speed of the subject's response is important in most testing, and the apparatus includes an automatic timer for each typewritten line of responses.

Various objects, advantages, and features of the invention will be apparent in the following description and claims considered together with the accompanying drawings forming an integral part of this specification, in which:

Figure 1:
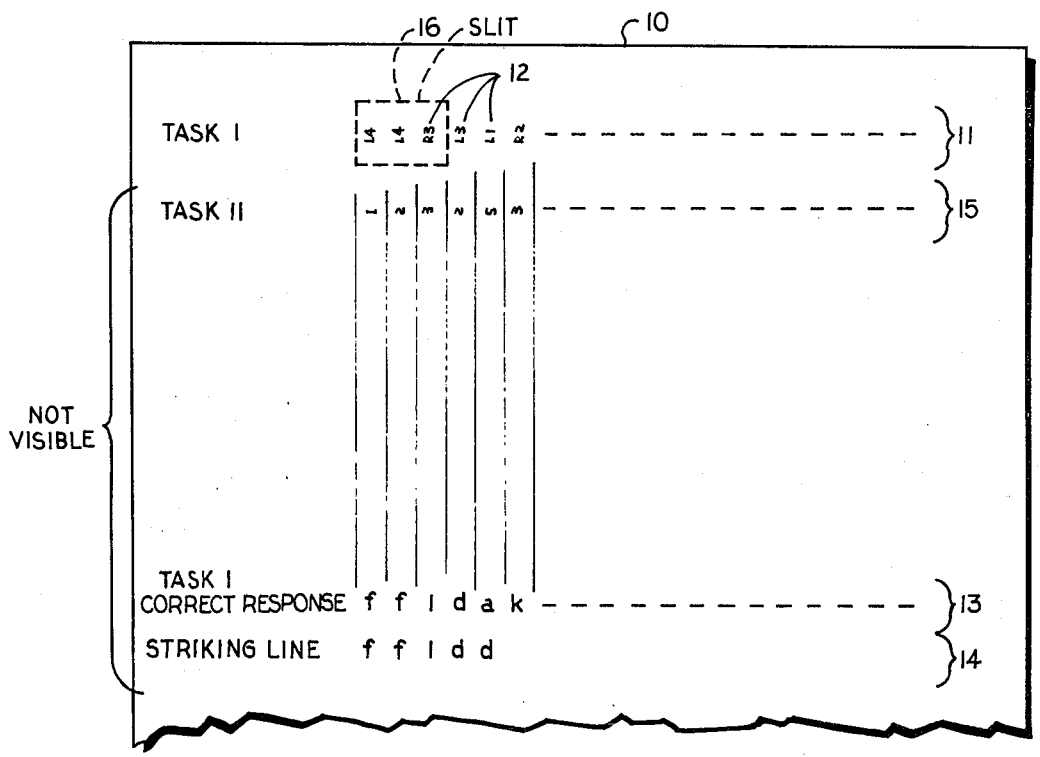
FIG. 1 is a plan view of a piece of paper upon which a task is inscribed, and spaced from this task is a striking line for a motor response.

Referring to FIG. 1, a sheet of paper 10 has a horizontal line 11, upon which is placed a series of indicia 12 after the legend "Task 1." The indicia 12 are in vertical columns, and the columns are in a horizontal array and may be small in size compared to the typewritten response. The sheet has to be rotated at ninety degrees to read these letters and numerals in their normal fashion and may be magnified. Spaced from the line 11 is a line 13 bearing the legend "Correct Response," after which there appears a series of letters. Below line 13, but closely adjacent thereto, is another horizontal line 14, which is the striking line of the typewriter; that is, the line on which a series of letters or numerals is normally typed in a horizontal line.

As will be described later, only a part of line 11 defining the task is visible to the operator. This is preferably done by masking off line 11 except for a slit area 16 shown in broken outline, which will reveal one or more task instructions or commands to the person using the apparatus. This same sheet 10 may have a number of tasks disposed thereon in either vertical columns or in normal horizontal array, and for each task there is a corresponding line similar to that of 13 for the correct response and line 14 for the striking line. Shown below "Task 1" 11 is "Task 2" 15. It uses a different stimulus-response code. It will be presented when the subject returns the carriage. In other words, one sheet of paper may have a plurality of task lines similar to line 11 and a plurality of response lines similar to line 14 for each task that appears, each maintaining a spacing and each being so spaced as not to interfere with other tasks and other striking lines.

Figure 2:
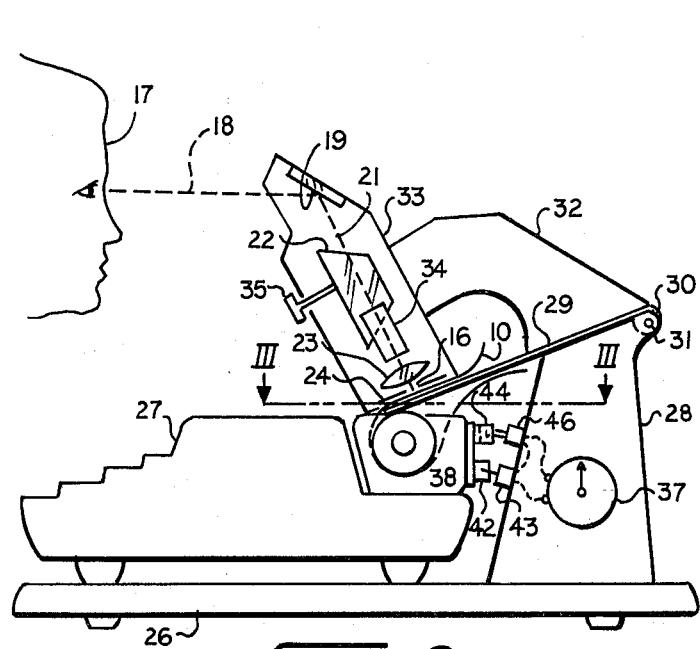
FIG. 2 is a schematic elevation view of the apparatus.

Referring to FIG. 2, a human subject 17 looks along the broken line or sight path 18 into a mirror 19, which deflects his line of sight downwardly along the broken line or sight path 21 through a Dove prism 22 and through a magnifying lens 23 to the paper 10 previously described. The paper 10 is visible, because the line of sight passes through a mask 24 in which the slit 16 is located as described with reference to FIG. 1.

The mask 24 is preferably made of translucent plastic in the form of a slide which is inserted into a holder. By use of the slide with the appropriate height, width, and location of slit, selection is made of the portion of the material prepared to exhibit any point of the material in the relative movement of the paper 10. The slit 16 may be a clear area in the translucent plastic or may be a window in the plastic. The translucent plastic allows ambient or artificial light to illuminate the slit area 16.

The entire apparatus is mounted on a base 26 on which is disposed a typewriter 27. The typewriter may be of any standard type; a moving-carriage type of keyboard is illustrated here. Also disposed on the base 26 is a pedestal 28 having an inclined paper support board 29 upon which the paper 10 lies, and this board is hinged at 30 for lifting to insert paper into the typewriter. Hinged to the upper right-hand corner of the pedestal 28 by means of hinge pin 31 is a support arm 32, which bears a housing 33 in which are located the mirror 19, the prism 22, the lens 23, and the mask 24. Also supported by the housing 33 is a light 34 for illuminating the part of the paper 10 visible through the mask slit 16. Secured to the prism 22 is a rotational handle 35, which may be manually actuated to rotate the prism to make the letters 12, which are in a vertical disposition, appear to be horizontal to the subject 17.

Disposed on the pedestal 28 is an electric clock 37 which times the period in which the subject 17 responds to the commands on a line of commands; for example, line 11 of FIG. 1. The clock 37 is actuated by the typewriter 27, which has, as viewed in FIG. 3, a reciprocating carriage 38, upon which is mounted a cylindrical rotatable platen 39. The carriage 38 is moved to the right as viewed by the subject 17, but will be in a downward direction as viewed in FIG. 3. This positions the paper on the platen 39 in placement for the beginning of a line starting from the left part of the paper and proceeding to the right in the normal reading direction. Disposed on the rear of the carriage 38 is a cam 42 which engages a leaf on a momentary switch 43 that is normally closed to hold the switch 43 open in this starting position of the carriage, so that current does not flow to the clock 37. Also disposed on the rear of the carriage 38, but at a different level is a second cam 45, which strikes an off-on or detent switch 46, which is closed by this movement of the carriage to the right (down in FIG. 3) to start a new line of typing.

When the first character is typed, the carriage 38 moves to the left (up in FIG. 3), closing the switch 43, which then admits current to the clock 37, allowing it to begin running. When the carriage 38 moves completely to the left, as viewed by the subject 17 (up in FIG. 3), a second cam 44 opens detent switch 46 in series with switch 43 to stop current to the clock 37, thus indicating the elapsed time that the subject took to type a full line on the typewriter 27. Cams 44 and 45 are at the same level to alternately close and open switch 46. During the carriage return to the starting position, no current is admitted to clock 37, because detent switch 46 has not yet been closed. When the carriage has almost reached its full return, cam 42 again opens switch 43. At the point of full return, the second cam 45, mounted above cam 42, closes detent switch 46. However, no current can flow to clock 37 until the subject makes the first key stroke of the next line to close momentary switch 43. The clock can therefore integrate the time periods for a number of striking lines 14.

Figure 3:
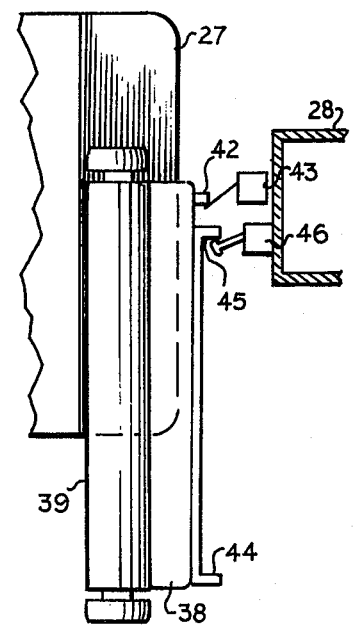
FIG. 3 is a sectional view taken along the line III—III of FIG. 2 to illustrate the clock switches.
Figure 4:
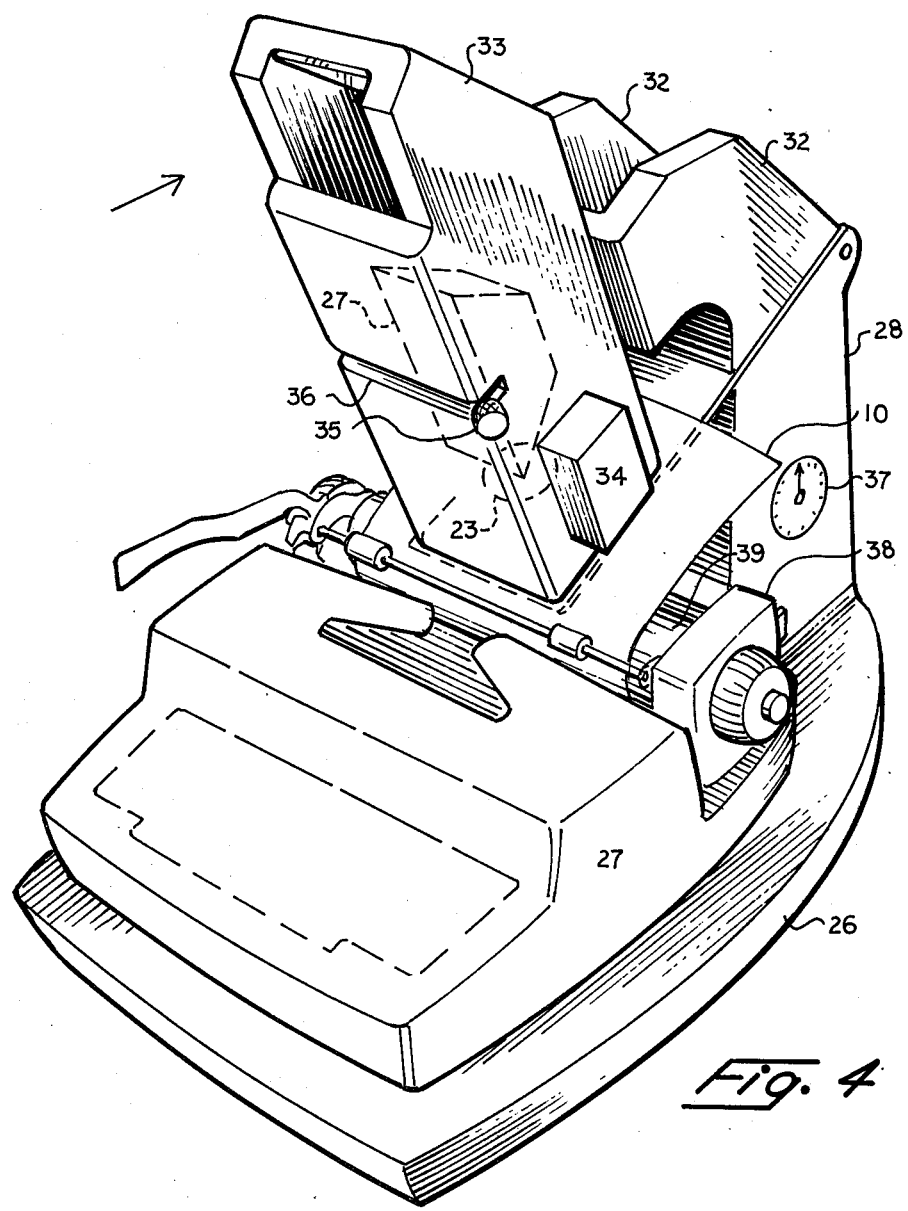
FIG. 4 is a three-dimensional view of the apparatus of FIG. 2.
Figure 5:
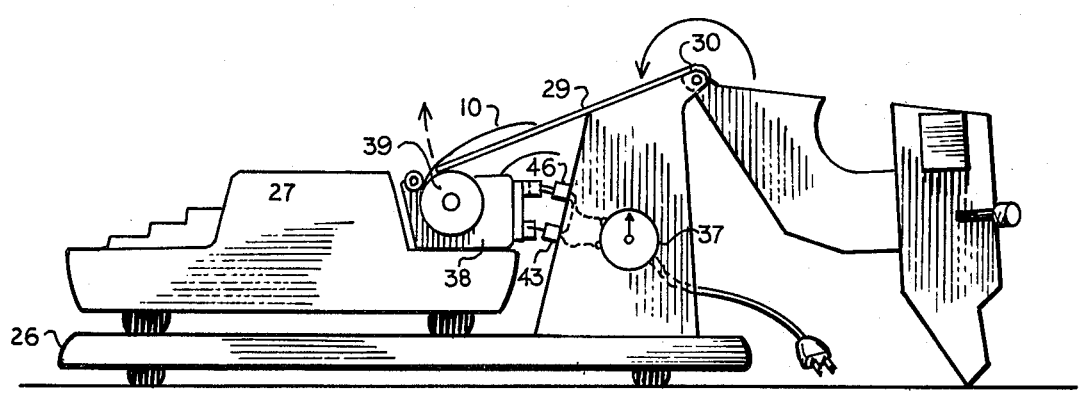
FIG. 5 is an elevation view of the apparatus of FIG. 1 with the upper part of the hinged apparatus pivoted to a downward position.

Referring to FIGS. 4 and 5, the three-dimensional view of the apparatus of FIGS. 2 and 3 is illustrated. It will be noted that the sheet of paper 10 is disposed over the platen 39, and the carriage 38 is shown in a middle position during the typing of a line. The housing 33 has a slot 36 formed therein through which the prism rotation handle 35 may rotate. Illustrated in FIG. 5 is the foldedover position of the apparatus, which is used for inserting fresh pieces of paper in the typewriter 27, and this may be easily done by lifting the board 29 about its hinge 30.

The operation of the apparatus for testing the subject 17 is as follows: The subject 17 peers through the apparatus of FIG. 2 and observes through the slit 16 of FIG. 1 three commands; namely, L4, L4, R3. He interprets these instructions or tasks or commands to mean to press first the left hand's fourth finger from the left once, and then for the second command to press it again, and then for the third command to press the right hand's third finger from the left. If these tasks are correctly accomplished, he will type the letters f, f, and l on the striking line 14. At each stroke of the typewriter, however, the slit 16 will move relative to the paper to the right exposing further commands, such as L3, L1, R2. As these commands are followed, the subject 17 will type d, a, and k. Illustrated on line 14 of FIG. 1 is a mistake in the fifth column wherein the subject typed a d instead of an a in response to the instruction L1. The grading of the response is readily done by comparing lines 13 and 14 of FIG. 1, line 13 containing the correct response and line 14 containing the response of the subject being tested. There it readily shows up that the fifth letter is a mistake, and the person grading the paper can readily pick this up and mark the paper accordingly.

In accomplishing the operation just described, the subject 17 looks into the mirror 19 through the prism 22 through the magnifying lens 23 and through the slit 16 in the mask 24 to view the paper 10; namely, line 11 of FIG. 1. The subject then types the correct response, and the carriage 38 of the typewriter moves to the subject's left, or up as viewed in FIG. 3. The cam 42 of FIG. 3 also moves upwardly (actually to the left), releasing the switch 43 so that it closes, supplying current to the clock 37, which thereupon records the time that the subject takes in answering the tasks. When the subject has completed a line of response by striking the typewriter keys and causing the carriage 38 to move to the subject's left, or up in FIG. 3, the cam 44 will strike the detent on-off switch 46, opening the circuit to the clock 37 and causing it to stop. The elapsed time for the particular line of response will then be indicated by the clock and can be entered into the test score of the subject 17.

The subject then strokes the typewriter carriage 38 to the right, which sets up a new task on a new line as indicated by the legend "Task 2" of FIG. 1. This presents a new striking line similar to that of 14 of FIG. 1, whereupon the subject responds to the commands of the new Task 2 and types his response thereon. The carriage return first causes cam 42 to open switch 43 and then causes cam 45 to close switch 46.

It will be noted in FIG. 1 that the Task 1 line 11 has the commands in a vertical orientation, even though the entire line 11 is horizontal. To present the commands in the horizontal orietation usually desired, the prism 22 is previously manually rotated by manually grasping the lever 35 and rotating it to the proper angle. The vertical commands will thereupon appear to be horizontal to the subject 17, enabling him to read off these commands in a normal fashion. Since the prism 22 may be rotated to any angle, it is not necessary to present the rows horizontally. They may remain vertical, be angled, or shown upside down. The miniaturized commands are rendered easy to read by the magnifier lens 23.

It will be obvious to those skilled in the art that this same apparatus may be used for paced commands. The subject can merely follow the commands or tasks set forth in the prepared paper, and successive responses can be paced either according to the subject's own pace or by regular signals by various clocks, etc. Alternatively, the carriage can be automatically advanced from one command to another by an external timer and the key advance rendered inoperative. In any case, the striking line is disposed a few inches below the task line on the prepared piece of paper that is inserted in the typewriter 27. The task displayed, of course, can be made more complicated. For example, associative learning tasks can be presented wherein the subject presses left or right forefinger according to which of two displayed response words is the correct word for the displayed stimulus word. The device can be used for short-term memory wherein a list of symbols is displayed, and the space bar is pressed on the typewriter to display a probe or question item of whether a particular item was on the list displayed. The left forefinger can then be pressed for a "yes" answer that the word was on the list or the right forefinger can be pressed for a "no" response. Other tasks which can be performed on the apparatus include concept-learning, perceptual judgement, sequence-learning, speed of repeated tapping with a finger of each hand, and visual search. In any of these types of use, it is apparent that the ability of the prism to rotate commands and use of a magnifying lens permits rather long vertical commands as they are placed on the prepared sheet of paper 10, wherein only a short response such as a single letter or numeral is all that is required. The terms "vertical columns" or "vertical commands" are used herein to include diagonal indicia.

In addition to its use in psychological testing and experimentation, the device may also be used for a variety of training purposes. For example, the literature suggests that apparatus of this type can be used as an exercise for older persons to retain mental agility or restore mental agility and rehabilitate after a stroke, etc. While the invention has been described with respect to a typewriter which types along horizontal lines, it is apparent that responses can be placed in vertical columns by use of a typewriter which easily rotates the platen to present a next striking space rather than causing relative movement to the right or left. Also, it will be apparent to those skilled in the art that various types of typewriters can be used, and those in which the paper does not reciprocate, but rather has a travelling impression-maker such as a ball which strikes the paper, can be used so long as there is a suitable mechanical connection between the moving ball and the slit in the mask 10.

It will be apparent to those skilled in the optical arts that the mirror functions to properly present materials viewed through the Dove prism, which has an inverting action. The mirror does, however, present the material in a convenient fashion. If the prepared material on the paper is in mirror image form, there is no need for the mirror. Any other prism or optical system can be used which gives the same result. For these and other reasons, I do not limit myself to the specific embodiment illustrated, but include within the scope of the following claims all variations and modifications that fall within the true spirit and scope of the invention.

I claim:
1. Apparatus for testing the visual-motor responses of human subjects who operate a keyboard device comprising:
   a. a typewriter having a horizontal striking line and a part that moves horizontally as the striking line is typed;
   b. a sheet of paper inserted into the typewriter and having a plurality of vertical commands in horizontal array that are miniature in size and therefore not easily readable, but visible to the subject along a sight path and also having a clear area along the striking line;
   c. optical means disposed in the sight path between the subject and the paper for rotating optically the commands so that they appear to the subject to be horizontal;
   d. a magnifier disposed in the sight path to enlarge the commands so that they are easily readable;
   e. a slitted mask disposed in the sight path to limit the number of commands visible to the subject;
   f. and means supporting said mask and connected to one of said typewriter or moving part of the typewriter, to obtain relative movement of the mask and paper as the typing progresses;
   whereby new commands are revealed to the subject as responses to commands are typed.

2. Apparatus for testing the visual-motor responses of human subjects who operate a keyboard device comprising:
   a. a typewriter having a horizontal striking line;
   b. a sheet of paper inserted in the typewriter and having a plurality of vertical commands in horizontal array and that are visible to the subject along a sight path and having a clear area along the horizontal striking line;
   c. optical means disposed in the sight path between the subject and the commands to rotate optically the commands so that they appear horizontal to the subject,
   whereby the subject may type his responses to the commands along the striking line of the paper.

3. Testing apparatus as set forth in claim 2 wherein the optical means provides an inverted image and a mirror is disposed in the sight path to erect the inverted image.

4. Testing apparatus as set forth in claim 2 wherein the commands on the paper are miniature in size and difficult to read because of their size, and an optical magnifier is disposed in the sight path to so increase the size of the commands as to be easily readable by the subject.

5. Testing apparatus as set forth in claim 2 wherein the typewriter has a part that moves as typing progresses along the striking line, and there is provided a clock, and cam means are connected to the moving part for controlling the clock to start the clock at the commencement of typing along a striking line and to stop the clock at the end of a striking line, to thereby measure the time of response to the commands.

6. Testing apparatus as set forth in claim 2 wherein a slitted mask is disposed in the sight path between the subject and the paper to reveal a selected area of the commands, and mechanical means are provided to create relative movement between the mask and the paper as the response is typed, to thereby limit the commands visible to the subject and reveal new commands as the typing progresses.

* * * * *